United States Patent [19]

Arenberg et al.

[11] Patent Number: 5,419,312
[45] Date of Patent: May 30, 1995

[54] MULTI-FUNCTION ENDOSCOPE APPARATUS

[75] Inventors: Irving K. Arenberg, Englewood, Colo.; Stephen T. Flock; Milton Waner, both of Little Rock, Ark.

[73] Assignee: Wildflower Communications, Inc., Englewood, Colo.

[21] Appl. No.: 50,555

[22] Filed: Apr. 20, 1993

[51] Int. Cl.⁶ ............................................. A61B 1/06
[52] U.S. Cl. .................................... 128/6; 128/4; 128/736; 128/748
[58] Field of Search ...................... 128/4–10, 128/664, 665, 693, 736, 741, 748, 772, 675; 385/117, 116; 606/15–16, 11; 604/20; 607/89, 93, 88; 73/356

[56] References Cited

U.S. PATENT DOCUMENTS

| | | | |
|---|---|---|---|
| 3,261,349 | 6/1966 | Wallace | 128/6 |
| 3,858,586 | 1/1975 | Lessen | 128/6 X |
| 3,888,237 | 6/1975 | Mori | 128/6 X |
| 4,016,761 | 4/1977 | Rozzell et al. | 73/356 |
| 4,364,629 | 12/1982 | Lang et al. | 385/117 X |
| 4,422,457 | 12/1983 | Hattori | 128/6 X |
| 4,423,727 | 1/1984 | Widran et al. | 128/7 X |
| 4,461,282 | 7/1984 | Ouchi et al. | 128/4 |
| 4,560,286 | 12/1985 | Wickersheim | 128/736 X |
| 4,569,335 | 2/1986 | Tsuno | 128/6 |
| 4,836,189 | 6/1989 | Allred, III et al. | 128/6 |
| 4,895,156 | 1/1990 | Schulze | 128/736 X |
| 4,927,226 | 5/1990 | Ortiz, Jr. | 606/11 X |
| 4,986,671 | 1/1991 | Sun et al. | 128/675 X |
| 4,995,396 | 2/1991 | Inaba et al. | 128/6 X |
| 5,090,959 | 2/1992 | Samson et al. | 128/6 X |
| 5,114,402 | 5/1992 | McCoy | 128/4 X |
| 5,121,740 | 6/1992 | Uram | 128/6 |
| 5,190,028 | 3/1993 | Lafferty et al. | 128/6 |
| 5,235,965 | 8/1993 | Hiroya | 128/6 |
| 5,268,082 | 12/1993 | Oguro et al. | 128/772 X |

FOREIGN PATENT DOCUMENTS

| | | | |
|---|---|---|---|
| 2743781 | 4/1978 | Germany | 128/6 |
| 2820239 | 11/1978 | Germany | 128/6 |
| 9215238 | 9/1992 | WIPO | 128/6 |

*Primary Examiner*—Richard J. Apley
*Assistant Examiner*—John Leubecker
*Attorney, Agent, or Firm*—Klaas, Law, O'Meara & Malkin

[57] ABSTRACT

A multi-function endoscope capable of insertion within a body cavity for treatment/diagnostic purposes. The endoscope includes a flexible probe having an optical fiber connected to a laser light source, an optical fiber bundle connected to an illuminating light source, and another optical fiber bundle with a focusing lens thereon connected to a viewing system. The probe further includes an optical fiber having a sensor system associated therewith for making temperature and fluid pressure measurements within the body cavity. Also included are fluid conduits through the probe, and detecting wires for receiving electrical potentials from body cavity tissues. Finally, the probe includes steering wires which, when moved, cause probe movement. The steering wires are moved using a manipulator system consisting of stepper motors connected to a computer controller.

12 Claims, 5 Drawing Sheets

MULTI-FUNCTION ENDOSCOPE APPARATUS

BACKGROUND OF THE INVENTION

The present invention generally relates to medical instruments, and more particularly to a multi-function, flexible endoscope apparatus designed for the diagnosis, treatment, and analysis of tissues within a body cavity.

In order to properly administer medical care to a patient, it is often necessary for a physician to conduct an internal investigation of the patient's body tissues and air/fluid cavities associated therewith. Frequently, this requires surgical entry into the patient's body cavities for diagnostic and treatment purposes. This may be accomplished through the use of an apparatus known as an "endoscope" which basically consists of a diagnostic, imaging, and therapeutic instrument designed for entry into various cavities of hollow organs/tissue regions to facilitate the observation and analysis thereof. The use of an endoscope to perform endoscopic examinations and treatment is important in a number of medical fields. For example, endoscopy of the inner ear may often be necessary in order to diagnose, measure, and/or treat a number of different otological conditions as generally described in Arenberg, I., "Overview of Inner Ear Disease", *The American Journal of Otology*, 8(3):189–194 (1987) which is incorporated herein by reference. For example, within the inner ear, it is often necessary to surgically insert multi-channel cochlear implants within patients who have experienced profound hearing loss caused by cochlear obstructions. The cochlea consists of a spiral tube in the inner ear which contains nerve endings essential for proper hearing. With respect to the cochlear implantation process, the use of a flexible fiber optic endoscope is disclosed in Balkany, T., "Endoscopy of the Cochlea During Cochlear Implantation", *Ann. Otol. Rhinol. Laryngol,* 99:919–922 (1990). Specifically, in this article, endoscopy was found to be helpful in visualizing obstructed cochlear segments, determining patency after the removal of cochlear obstructions, and identifying normal cochlear structures in order to better seat cochlear implants.

There are a wide variety of different medical applications for which endoscopy is appropriate and necessary. Furthermore, many types of endoscopes have been produced which include a variety of different features. For example, U.S. Pat. Nos. 4,589,404 and 4,754,328 to Barath et al. disclose a laser endoscope having optical fibers designed for laser light delivery and an optical fiber bundle for viewing images from within a body cavity.

U.S. Pat. No. 4,604,992 to Sato discloses an endoscope system which includes a CCD (charge coupled device) camera designed to supply video images to a television monitor. The endoscope system further includes fiber optical systems connected to illumination and laser light delivery sub-systems. A similar CCD endoscope system is described in U.S. Pat. No. 4,803,562 to Eino and U.S. Pat. No. 4,473,841 to Murakoshi et al.

U.S. Pat. No. 4,928,695 to Goldman et al. discloses a medical treatment apparatus which includes an optical fiber for illuminating tissue, an optical fiber for delivering laser light (used to treat the tissue), an electrode for producing an electrical field at or near the tissues of concern, and an optical phase conjugator unit for improving the quality of visual images generated within the system.

U.S. Pat. No. 4,770,653 to Shturman involves a catheter system which includes an imaging optical fiber, a laser delivery fiber, internal torque wires, and various conduits therein.

U.S. Pat. No. 4,615,332 to Buess et al. discloses a binocular endoscope system having a plurality of passages therein, as well as a pressure sensor and fiber optic viewing system.

Other endoscope-type devices are illustrated and described in U.S. Pat. Nos. 4,702,571 to Barber; 4,061,135 to Widran et al; and 4,901,142 to Ikuno et al.

The present invention as described herein represents a flexible endoscope device which is substantially different from the foregoing devices. Specifically, the invention satisfies an existing need for an endoscope system which is especially suitable for use in very small body cavities (e.g. within the inner ear) wherein the endoscope system includes a multitude of functional capabilities ranging from temperature and fluid pressure sensing means to highly advanced viewing, imaging, and micro-manipulation sub-systems. Likewise, the invention enables therapeutic laser light to be accurately delivered to internal body cavities and tissue regions as desired. Accordingly, the present invention represents an advance in the art of medical instrument design, as described in greater detail below.

SUMMARY OF THE INVENTION

It is an object of the present invention to provide an improved, multi-functional endoscope apparatus.

It is another object of the invention to provide an improved, multi-functional endoscope apparatus which is capable of insertion within body cavities of relatively small size.

It is another object of the invention to provide an improved, multi-functional endoscope apparatus which is especially suited for use in the inner ear of a human subject.

It is another object of the invention to provide an improved, multi-functional endoscope apparatus which includes a specialized system for illuminating the interior of a body cavity and directing the resulting images outwardly from the cavity for observation.

It is another object of the invention to provide an improved, multi-functional endoscope apparatus which includes a sub-system for delivering laser light to the body cavity for treatment purposes in a safe and effective manner for both the patient and treating physician.

It is a further object of the invention to provide an improved, multi-functional endoscope apparatus which incorporates a specialized sub-system for automatically sensing temperature and fluid pressure levels within a body cavity.

It is a still further object of the invention to provide an improved, multi-functional endoscope apparatus which includes a sub-system for sensing electrical potentials generated within tissue materials inside a body cavity, including electrical potentials generated within single cells (e.g. hair cells in the human ear).

It is a still further object of the invention to provide an improved, multi-functional endoscope apparatus which is readily manipulated within a body cavity using a sophisticated and precise remote control system.

It is an even further object of the invention to provide an improved, multi-functional endoscope apparatus which incorporates all of the foregoing systems and sub-systems in a highly compact unit to produce an endoscope apparatus which is usable in a wide variety of medical applications.

In accordance with the foregoing objects, the present invention involves a unique, multi-functional endoscope apparatus which is capable of insertion within a body cavity for treatment, measurement, analytical, and diagnostic purposes. The endoscope apparatus basically includes a flexible probe having a medial portion, a first end, and a second end, with the first end of the probe being specifically sized for placement within a selected body cavity. Operatively connected to the probe is laser light supply means for delivering laser light to the probe. Further provided within the medial portion of the probe is first light transmission means for receiving laser light from the laser light supply means. In a preferred embodiment, the first light transmission means consists of at least one elongate primary optical fiber positioned within the medial portion of the probe. The primary optical fiber is preferably movable within the medial portion of the probe, and includes a first end and a second end. The first end is positioned at the first end of the probe. The second end extends outwardly from the second end of the probe, and is operatively connected to the laser light supply means.

In order to illuminate the body cavity in which the probe is inserted, the endoscope apparatus further includes primary illumination means operatively connected to the probe for delivering illuminating light thereto. Provided within the medial portion of the probe is second light transmission means which is operatively connected to the primary illumination means in order to receive illuminating light therefrom. In a preferred embodiment, the second light transmission means consists of a primary bundle of individual optical fibers having a first end and a second end. In a preferred embodiment, the first end of the primary bundle is positioned at the first end of the probe. The second end of the primary bundle extends outwardly from the second end of the probe, and is operatively connected to the primary illumination means. The primary bundle of optical fibers enables light from the primary illumination means to be delivered to the body cavity for viewing purposes as described in greater detail below.

Next, third light transmission means is proved within the medial portion of the probe for receiving visual images from the body cavity. Such images are generated by the illuminating light delivered from the second light transmission means into the body cavity. In a preferred embodiment, the third light transmission means consists of a secondary bundle of optical fibers which is operatively connected to observation means (e.g. a binocular microscope, conventional television monitor, three-dimensional television monitor, or comparable apparatus). The secondary bundle of optical fibers specifically includes a first end and a second end. The second end extends outwardly from the second end of the probe, and is operatively connected to the observation means. In a preferred embodiment, the first end extends slightly outward from the first end of the probe and includes a transparent cap member secured thereto which functions as a lens for directing illuminating light/visual images into the secondary bundle of optical fibers. In addition, protection means is provided for preventing the passage of laser light from the laser light supply means into the observation means (e.g. binocular microscope or television monitor) via the secondary bundle of optical fibers when the laser light supply means is in operation.

Next, the endoscope apparatus of the present invention includes sensing means for detecting temperature and fluid pressure levels within the selected body cavity. In a preferred embodiment, the sensing means includes a secondary illumination means for delivering additional light into and through the probe. Also included is fourth light transmission means which preferably consists of at least one secondary optical fiber (having a first end and a second end) which is movably positioned within the medial portion of the probe. The first end of the secondary optical fiber is positioned at the first end of the probe and, in one embodiment, has at least one liquid crystal secured thereto.

The liquid crystal (when positioned within the selected body cavity) permits differing amounts of light to be reflected therefrom, depending on temperature and fluid pressure conditions within the body cavity. The second end of the secondary optical fiber extends outwardly from the second end of the probe, and is operatively connected to the secondary illumination means. To measure temperature and pressure levels within the body cavity, light from the secondary illumination means is directed through a one-way mirror into the second end of the secondary optical fiber. The light then passes through the secondary optical fiber and strikes the liquid crystal. Part of this light is reflected by the liquid crystal back toward the second end of the secondary optical fiber. The amount of reflected light is dependent upon the temperature and fluid pressure conditions within the body cavity. The reflected light then leaves the secondary optical fiber and strikes the one-way mirror. The one-way mirror is positioned at an angle so that the reflected light is directed downwardly. The reflected light then passes into monitoring means for detecting and quantifying the reflected light. The resulting data may thereafter be appropriately correlated to determine temperature and fluid pressure levels within the body cavity.

In an alternative embodiment, the sensing means will include a portion of fluorescent material affixed to the first end of the secondary optical fiber instead of the liquid crystal. The remaining portions of the sensing system described above will remain the same. In operation, light from the secondary illumination means is directed through the one-way mirror into the second end of the secondary optical fiber. The light then passes through the secondary optical fiber and strikes the fluorescent material. As a result, fluorescent light is generated which travels back through the secondary optical fiber toward the second end thereof. The magnitude and spectrum of the fluorescent light generated by the fluorescent material is dependent upon the temperature and fluid pressure conditions within the body cavity. The fluorescent light then leaves the secondary optical fiber and strikes the one-way mirror which is again positioned at an angle. As a result, the fluorescent light is directed downwardly, preferably through at one conventional fluorescent filter known in the art and into the monitoring means.

The endoscope apparatus of the invention further includes a variety of additional sub-systems for performing various other functions. For example, the probe of the endoscope includes fluid transmission means therein for delivering fluid materials (e.g. liquids and/or gases) to and from the body cavity through the probe. The fluid transmission means may specifically be used to deliver medicines to the body cavity, withdraw collected bodily fluids from the body cavity, and/or remove various gases from the body cavity. In a preferred embodiment, the fluid transmission means consists of at least one continuous passageway through the probe from the first end to the second end thereof.

The probe also includes tissue potential sensing means for receiving electrical potentials from tissue materials (e.g. down to single cells) within the body cavity in which the probe is positioned. The tissue potential sensing means preferably consists of at least one elongate primary wire member having a first end and a second end. Each primary wire member is movably positioned with the medial portion of the probe so that at least a portion of the first end of each primary wire member may be extended outwardly from the first end of the probe. The second end of each primary wire member extends outwardly from the second end of the probe, and is operatively connected to detection means for measuring and analyzing electrical potentials received from the tissue materials in the body cavity.

Finally, the endoscope apparatus includes steering means for manipulating and moving the probe within the selected body cavity. The steering means preferably consists of a plurality of elongate secondary wire members positioned equidistantly from each other within the medial portion of the probe. Each of the secondary wire members includes a first end and a second end. The first end of each secondary wire member is preferably secured to the first end of the probe. The second end of each secondary wire member extends outwardly from the second end of the probe, and is operatively connected to micro-manipulator means (e.g. a computer-controlled stepper motor adjustment system). The exertion of force by the manipulator means on the second end of each secondary wire member causes corresponding movement of the entire probe within the body cavity, thereby allowing the position of the probe to be accurately controlled.

The present invention represents a highly advanced endoscope system with multi-functional capabilities. These and other objects, features, and advantages of the invention shall be described below in the following Brief Description of the Drawings and Detailed Description of Preferred Embodiments.

DETAILED DESCRIPTION OF PREFERRED EMBODIMENTS

Figure 1:
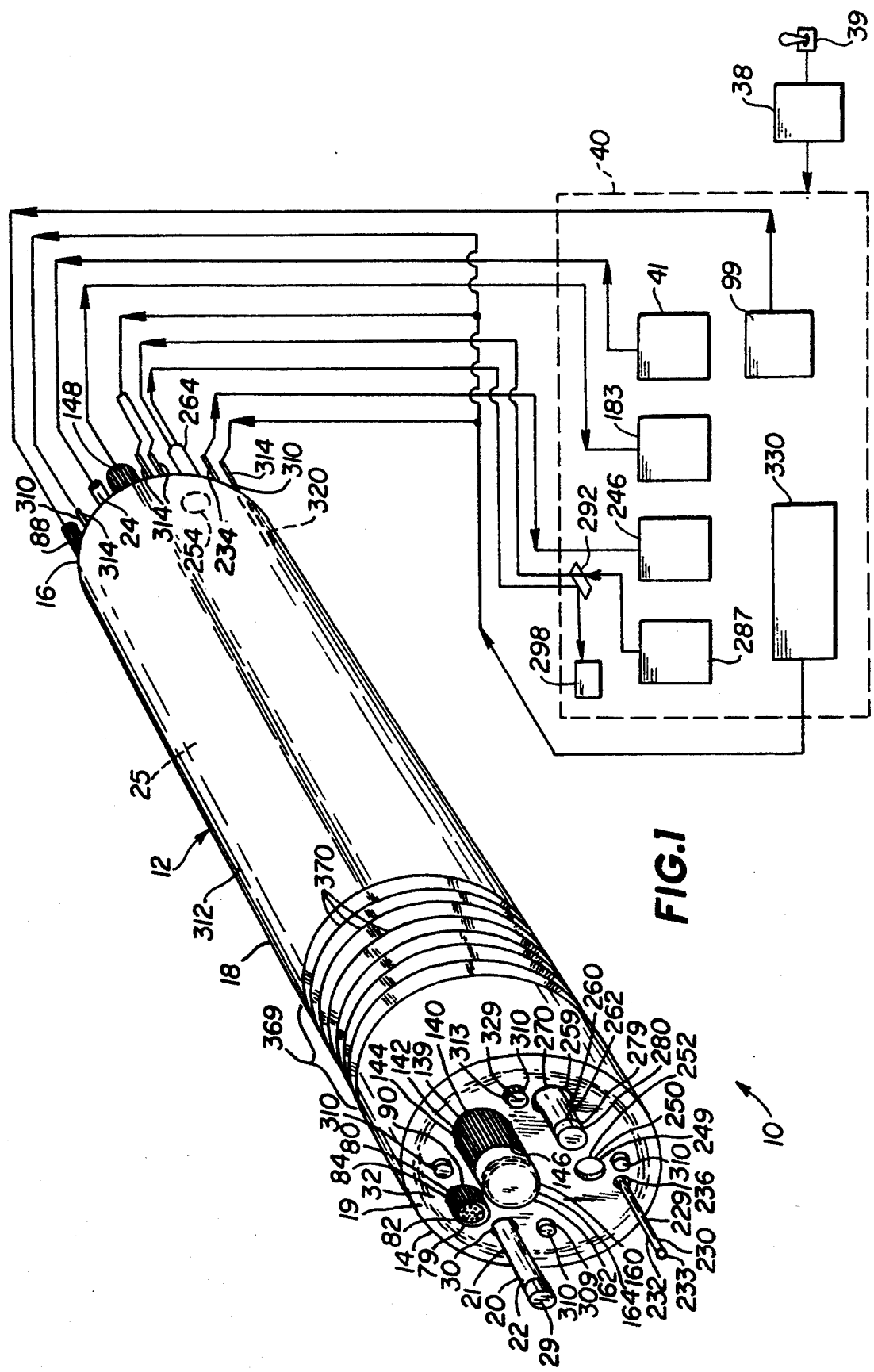
FIG. 1 is a schematic view of the endoscope apparatus of the present invention and sub-systems associated therewith wherein an enlarged front perspective view of the endoscope probe is schematically illustrated.

The present invention represents an advanced, multi-functional endoscope apparatus which is suitable for a wide variety of medical applications. The endoscope apparatus described herein is especially appropriate for diagnostic/therapeutic use in small body cavities. For example, the endoscope apparatus of the invention is ideally suited for use in the inner ear of a human subject. Entry into the inner ear may be accomplished surgically using a variety of techniques, including but not limited to the following procedures: (1) entry through the endolymphatic sac via a mastoidectomy approach; (2) entry through the round window membrane via a tympanomeatal flap; (3) entry through the oval window via stapedectomy or stapedotomy; (4) entry via bony vestibulostomies or cochleostomies (e.g. into one or more of the semicircular canals, into the vestibule, or into any turn of the cochlea); or (5) entry into the cochlear aqueduct/perilymphatic fluid compartments via a suboccipital craniotomy. The foregoing approaches may be used independently or in any combination thereof. They effectively enable the probe of the endoscope apparatus to observe, analyze, and treat various tissues within the inner ear. However, the present invention shall not be limited to exclusive use of the foregoing techniques which are provided for example purposes only.

With respect to the treatment, measurement and/or analysis of inner ear tissues, the endoscope apparatus may be used for a wide variety of purposes. One of these purposes involves the visualization of Reissner's membrane in the cochlear duct to analyze the distention thereof. Pressure and/or temperature changes in the endolymph/perilymph associated with endolymphatic hydrops may also be determined. The resulting data involving pressure changes and membrane distention may then be correlated using three dimensional vector electrocochleography and three dimensional video monitoring without glasses. Electrocochleography (hereinafter designated as "ECoG") is a known technique for measuring tissue electrical potentials which basically involves measurement of the whole nerve-cochlear action potential (hereinafter "AP"). Alternatively, ECoG can be used to measure individual hair cell electrical activity. ECoG can further be used to measure the summating potential (hereinafter "SP") within the inner ear in response to externally generated clicks, tone bursts, and/or pips. The SP is basically a D.C. distortion potential which can indicate the amount of distortion in the cochlear duct associated with endolymphatic hydrops or other changes in the inner ear. The relative amount of distortion may be expressed either as an SP/AP ratio (in response to externally-generated clicks, etc.), or as an absolute measurement in response to externally-generated tone bursts and the like. Cochlear microphonics can also be measured as well as otoacoustic emissions (hereinafter "OAE") in order to assess hair cell function or dysfunction. Further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, Colo. (U.S.A.) Jul. 29-Aug. 4, 1990 as reported in *Inner Ear Surgery*, edited by I. Kaufman Arenberg, Kugler Publications, Amsterdam/New York, pp. 241-247 (1991) which is incorporated herein by reference.

Another suitable use for the probe apparatus of the present invention involves the evaluation, measurement, and treatment (using laser energy) of adhesions within the inner ear (e.g. the lysis of fibrons/inflammatory adhesions). The probe apparatus may also be used to evaluate the anatomic position of the utriculoendolymphatic valve of Bast and, if deficient or incompetent, laser it into a better functional position.

Finally, the probe apparatus may be used to create discrete diameter otic and perotic shunts or fistulae anywhere in the membranous labyrinth on a temporary or long term basis.

Further general information regarding endoscopy within the human inner ear is described in Balkany, T., "Endoscopy of the Cochlea During Cochlear Implantation", *Ann. Otol. Rhinol. Laryngol*, 99:919-922 (1990) which is incorporated herein by reference. While the present invention as described below shall be discussed with primary reference to use within the inner ear, there are a wide variety of other body cavities/tissues which may be effectively treated/examined using the invention. For example, the present invention has substantial prospective utility with respect to the middle ear, Eustachian tube, renal tissues/organs (e.g. the kidneys), the medial portions of the eye, and the examination/analysis of tissues associated with the central nervous system (e.g. the brain and spinal cord). Furthermore, the endoscope apparatus of the invention may be useful in the analysis and treatment of vascular structures including those as small as capillaries and arterioles. Thus, the endoscope apparatus described herein shall not be limited exclusively to use within the inner ear and associated tissues.

With reference to FIG. 1, the endoscope apparatus of the present invention is schematically illustrated and generally represented at reference number 10. The endoscope apparatus 10 includes a substantial number of individual sub-systems, each of which will be described individually below.

As shown in an enlarged, schematic format in FIG. 1, the endoscope apparatus 10 first includes a probe 12 which comprises the basic functional element of the apparatus 10. At least a portion of the probe 12 is designed for insertion within the selected body cavity (e.g. the inner ear) during a medical procedure. In a preferred embodiment, the probe 12 is substantially circular in cross section and comprised of rubber (e.g. synthetic or natural) or other comparable resilient material known in the art. The selected construction material should have an index of refraction which is less than the refractive index of the optical fiber materials used in the probe 12 as described below. Using the foregoing materials, the probe 12 may be produced through conventional molding/fabrication processes known in the art. Specifically, if made of rubber, plastic or the like, the probe 12 may (in one embodiment) be molded around the various components to be used therein as described below. While the dimensions of probe 12 may be selectively varied depending on the ultimate use for which it is intended, the probe 12 preferably has a uniform diameter of about 300-500 microns which is suitable for use in the inner ear of a human subject, and is optimally about 20-30 cm in length. However, the probe 12 may be longer than 20-30 cm, depending on its intended use. Accordingly, it should be noted that the dimensions of various structures and components set forth herein are for example purposes only, and the present invention shall not be limited to any specific numerical dimension values.

With continued reference to FIG. 1, the probe 12 includes a first end 14, a second end 16, and a medial portion 18 positioned between the first end 14 and the second end 16. During insertion of the probe 12 within a body cavity, the first end 14 will enter and be entirely placed within the cavity. Accordingly, the dimensions described above will enable the first end 14 to be readily inserted, especially with respect to the inner ear. As illustrated in FIG. 1, the peripheral edges 19 at the first end 14 of the probe 12 are preferably smoothed and rounded in order to prevent any tissue damage during entry of the first end 14 of the probe 12 into the selected body cavity.

With continued reference to FIG. 1, the various internal components of the probe 12 will now be described. As illustrated in FIG. 1, the probe 12 includes first light transmission means 20 which is designed to deliver laser light from the probe 12 into the selected body cavity. The delivered laser light may be used for a variety of medical purposes including but not limited to tissue/cell ablation or vaporization, tissue welding, photodynamic therapy, lysis of adhesions, and the like. In a preferred embodiment, the first light transmission means consists of an elongate primary optical fiber 21 having a first end 22 and a second end 24. An exemplary optical fiber 21 suitable for laser light delivery as described herein will consist of a high-power silica-clad quartz fiber which is known in the art and commercially available from Schott Fiber Optics, Inc. of Southbridge, Mass. (U.S.A.). If the optical fiber 21 will be used in connection with infra-red laser light, the internal structure of optical fiber 21 should not include any water therein. Extraneous water within the internal structure of the optical fiber 21 will absorb infra-red laser light and diminish the ability of the optical fiber 21 to effectively transmit such laser light into the selected body cavity.

As illustrated in FIG. 1, the first end 22 of the optical fiber 21 is positioned adjacent the first end 14 of the probe 12 so that laser light passing through the optical fiber 21 may be delivered from the first end 14 of the probe 12 into the selected body cavity. If high power laser light densities are required, the first end 22 of the optical fiber 21 may optionally include a conventional glass fixed-focus microlens 29 (FIG. 1) of a type well-known in the art which is affixed to the first end 22. Alternatively, the microlens 29 may consist of a commercially available sapphire tip available from Surgical Laser Technologies of Philadelphia, Pa. (U.S.A.). Affixation of the microlens 29 to the first end 22 of the probe 12 may be accomplished using conventional adhesive materials (e.g. a composition commercially sold under the name Lens Bond TM by Summers Laboratories of Fort Washington, Pa. (U.S.A.)). The microlens 29 may ultimately be used to focus the delivered laser light down to a small spot within the selected body cavity.

As illustrated in FIG. 1, the optical fiber 21 is positioned within the interior region 25 of the medial portion 18 of the probe 12 by insertion thereof into a passageway 30 of uniform diameter which extends entirely through the medial portion 18 of the probe 12 from the first end 14 to the second end 16. The passageway 30 has a preferred uniform diameter of about 45–150 microns. The optical fiber 21 preferably has a uniform diameter which is less than that of the passageway 30 so that the optical fiber 21 may be selectively movable within the medial portion 18 of the probe 12. In a preferred embodiment, the diameter of the optical fiber 21 will be about 20–100 microns, with a clearance of about 25–50 microns between the optical fiber 21 and the interior walls of the passageway 30. This will enable the first end 22 of the optical fiber 21 to be moved outwardly from the end face 32 of the first end 14 of the probe 12 as shown in FIG. 1. Preferably, this configuration will allow the first end 22 of the optical fiber 21 to be moved outwardly to a distance of about 1–10 mm from the end face 32 of the probe 12 so that laser light passing through the optical fiber 21 may be more accurately applied to specific tissue zones within the selected body cavity. Movement of the optical fiber 21 may be accomplished through the use of a conventional stepper motor unit 34 (FIG. 3) operatively connected to roller units 35 (e.g. made of rubber or the like) which frictionally communicate with portion 36 of the optical fiber 21 adjacent the second end 24 thereof as schematically illustrated in enlarged format in FIG. 3. Selective operation of the stepper motor unit 34 causes movement of the roller units 35 which correspondingly move the optical fiber 21. The stepper motor unit 34 is of a type which is well known in the art. For example, an exemplary stepper motor unit 34 which may be used herein in accordance with the present invention is commercially available from Superior Electric of Bristol, Conn. (U.S.A.). The stepper motor unit 34 is preferably operated and controlled using a microcomputer 38 (e.g. a microcomputer manufactured by Futura/2000 of Little Rock, Ariz. (U.S.A.), model number 486DX2/66) to which a variable manual controller 39 (e.g. conventionally known as a "joystick") is connected. All of these components (e.g. the stepper motor unit 34, microcomputer 38 and variable manual controller 39) are commercially available components which are well known in the art and may be readily configured and operated by the endoscope user. Furthermore, the present invention shall not be limited to the foregoing components and arrangements thereof which are described above for example purposes.

Figure 3:
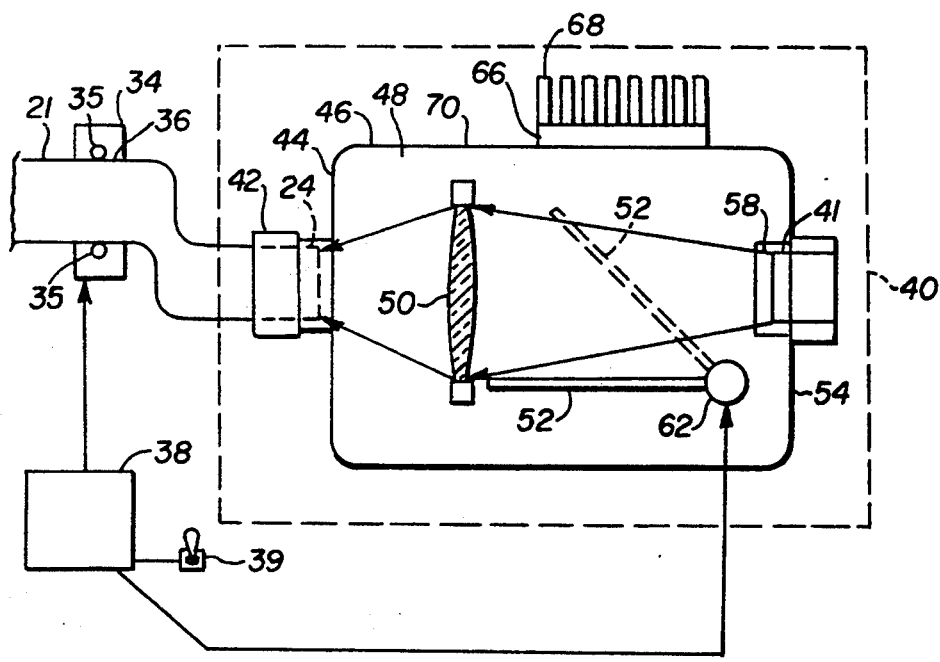
FIG. 3 is a schematic illustration of the laser light supply means and associated components which are used to supply laser light to the probe of FIG. 1.

As shown in FIGS. 1 and 3, the second end 24 of the optical fiber 21 extends outwardly from the second end 16 of the probe 12 and terminates within a connection box 40. The second end 24 is thereafter operatively connected to laser light supply means 41 (FIGS. 1 and 3) within the connection box 40 so that laser light may be effectively delivered to the selected body cavity through the optical fiber 21. As schematically illustrated, the second end 24 of the optical fiber 21 is secured using a conventional connector unit 42 (e.g. a standard SMA connector commercially available from Allied Signal (Amphenol Products Division) of Lisle, Ill. (U.S.A.)) to wall 44 of a chamber 46 (shown schematically and in cross-section in FIG. 3). Within the interior 48 of the chamber 46, a focusing lens 50 is provided which is capable of movement along X, Y, and Z axes. In a preferred embodiment, the lens 50 will consist of a conventional spherical coupling lens or aspheric lens having an F# equal to ½(NA) wherein NA is defined as the "numerical aperture" which is equivalent to the sine of the vertex angle of the cone of meridional rays that can enter the optical fiber 21. The lens 50 may also be coated with a conventional anti-reflective material (e.g. $MgF_2$).

Also included is a pivotally rotatable mirror 52, the function of which will be described below. Operatively secured to wall 54 of the chamber 46 is laser light supply means 41 in the form of a laser light source 58. The laser light source 58 may consist of a wide variety of commercially available laser light units, including but not limited to Nd:YAG, Ho:YAG, Ar, or diode units known in art which are available from, for example, Candela Laser Corp. of Wayland, Mass. (U.S.A.). Likewise, the laser light source 58 may also be selected from a variety of tunable dye laser systems which are generally well known in the art.

In use, the laser light source 58 directs laser light through the lens 50 and into the second end 24 of the optical fiber 21. The diameter of the resulting focused beam of laser light from the laser light source 58 should be about equal to the diameter of the optical fiber 21 for best results. During laser light delivery in this manner, the mirror 52 will be adjusted (either manually or automatically through the use of microcomputer 38 which is operatively connected to a standard solenoid 62) so that it is horizontally oriented and out of the laser light path as illustrated in FIG. 3. Should it be necessary for safety reasons or otherwise to immediately interrupt the delivery of laser light into optical fiber 21 without deactivating the laser light source 58, the mirror 52 may be positioned so that it blocks the laser light path as shown in phantom lines in FIG. 3. In a preferred embodiment, to interrupt the delivery of laser light, the mirror 52 will preferably be positioned (either manually or automatically) at about a 45° angle as illustrated so that the laser light is directed upwardly into a laser beam dump 66 of conventional construction having cooling fins 68 thereon. The beam dump 66 is positioned adjacent top wall 70 of the chamber 46. It is preferably made of a durable, heat-resistant metal (e.g. aluminum), and is designed to absorb thermal energy from the laser light. In this regard, the mirror 52 functions as protection means for preventing the delivery of laser light through the optical fiber 21 at undesired times as described in greater detail below.

Next, as shown in FIG. 1, the probe 12 further includes second light transmission means 79 for delivering illuminating light from the probe 12 into the selected body cavity. The illuminating light enables the probe operator to obtain a precise view of the medial portions of the selected body cavity. As illustrated in FIG. 1, the second light transmission means 79 preferably consists of a primary bundle 80 of individual optical fibers 82, with the primary bundle 80 having a first end 84 and a second end 88. In the illustrated embodiment, the first end 84 of the primary bundle 80 extends slightly outward from the end face 32 of the first end 14 of the probe 12 as illustrated in FIG. 1. As indicated above, the primary bundle 80 is preferably comprised of multiple (e.g. about 10–1000) individual glass optical fibers 82 which are commercially available from a variety of sources including but not limited to Schott Fiber Optics, Inc. of Southbridge, Mass. (U.S.A.). In an alternative embodiment, a single fiber (not shown) may be used in place of the primary bundle 80, although a bundle of individual optical fibers is preferred because it is easier to couple to a source of illuminating light (as described below) and will carry more light than a single fiber.

Figure 4:
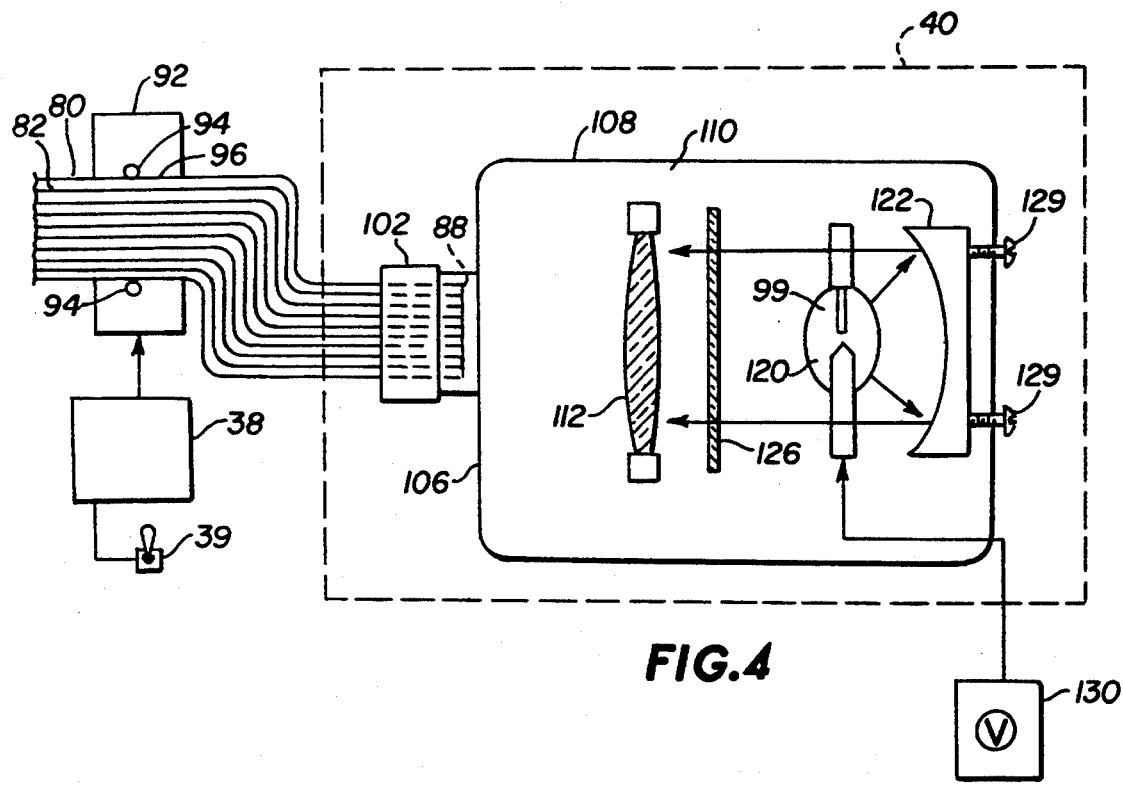
FIG. 4 is a schematic illustration of the primary illumination means and associated components which are used to supply illuminating light to the probe of FIG. 1.

The primary bundle 80 may be either round or elliptical, and is adapted for receipt within the medial portion 18 of the probe 12 through a passageway 90 of uniform diameter which extends entirely through the medial portion 18 of the probe 12 from the first end 14 to the second end 16. The passageway 90 may be round or elliptical, depending on the selected configuration of the primary bundle 80. In the embodiment illustrated in FIG. 1, the passageway 90 is substantially round, having a uniform diameter of about 50-200 microns. Likewise, in the embodiment of FIG. 1, the primary bundle 80 is substantially round, having a uniform diameter of about 100-300 microns. Preferably, the diameter of the primary bundle 80 should be about equal to or slightly greater than the diameter of the passageway 90 so that the primary bundle 80 may be urged inwardly into the passageway 90 and fixedly retained therein through resilient frictional engagement between the primary bundle 80 and the interior walls (not shown) of the passageway 90. An adhesive (e.g. conventional autologous fibrin glue as generally described in U.S. Pat. No. 4,874,368 to Miller et al.) may also be used to secure the primary bundle 80 within the passageway 90. In the alternative, the primary bundle 80 may be movable within the passageway 90 in the same manner described above regarding optical fiber 21 by making the diameter of the passageway 90 slightly larger than the diameter of the primary bundle 80 (e.g. so that there is a clearance between the primary bundle 80 and the interior walls of the passageway 90 of about 75-225 microns.) Movement of the primary bundle 80 may then be accomplished through the use of a conventional stepper motor unit 92 (FIG. 4) operatively connected to roller units 94 (e.g. made of rubber or the like) which frictionally communicate with portion 96 of the primary bundle 80 adjacent the second end 88 thereof as illustrated in FIG. 4. Selective operation of the stepper motor unit 92 causes movement of the roller units 94 which correspondingly move the primary bundle 80. The stepper motor unit 92 is preferably operated and controlled using microcomputer 38 and variable manual controller 39 as described above which are operatively connected to the stepper motor unit 92. It should also be noted that the stepper motor unit 92 and the roller units 94 may be of the same general type as the stepper motor unit 34 and roller units 35 described above.

Furthermore, it is preferred that the primary bundle 80 be non-coherent. The term "non-coherent" as used herein shall involve a situation in which the orientation of the fibers 82 (relative to each other) at the first end 84 of the primary bundle 80 is different from the orientation of the fibers 82 at the second end 88 of the bundle 80. While the primary bundle 80 may also be coherent, a non-coherent bundle 80 is preferred in that it functions with equal effectiveness at a lower construction/purchase cost.

In the illustrated embodiment wherein the primary bundle 80 is fixedly secured within the passageway 90, the first end 84 extends slightly outward from the end face 32 of the first end 14 of the probe 12 as indicated above. With reference to FIGS. 1 and 4, the second end 88 of the primary bundle 80 extends outwardly from second end 16 of probe 12, and terminates within connection box 40 (FIG. 4). The second end 88 is thereafter operatively connected to primary illumination means 99 (FIG. 1) within the connection box 40 so that illuminating light (e.g. white light) may be effectively delivered to the selected body cavity through the primary bundle 80. As schematically illustrated in FIG. 4, the second end 88 of the primary bundle 80 is operatively connected using a conventional connector unit 102 (e.g. a standard SMA connector or comparable device) to wall 106 of a chamber 108 (shown schematically and in cross-section in FIG. 4). Positioned within the interior 110 of the chamber 108 is a focusing lens 112 which is preferably capable of movement in the Z axis. The lens 112 may, in a preferred embodiment, be aspheric or a fiber-coupling sphere, with both structures being well-known in the art. Likewise, the lens 112 is preferably coated with a conventional anti-reflective material (e.g. $MgF_2$). In addition, the lens 112 will have an F# equal to $\frac{1}{2}$(NA), wherein NA is defined in the same manner described above relative to lens 50.

The primary illumination means 99 provided within the chamber 108 basically consists of a conventional illuminating light source 120 in the form of an arc lamp (Xe) or other comparable illumination device (e.g. a halogen lamp known in the art). The light source 120 as illustrated in FIG. 4 is positioned within the chamber 108 directly ahead of a convex mirrored reflector unit 122 of a type which is likewise well known in the art. Preferably positioned between the light source 120 and the lens 112 is a conventional infra-red optical filter 126 which is fixedly secured within the chamber 108 as shown. The filter 126 is designed to substantially eliminate infra-red thermal energy from the illuminating light which passes into the primary bundle 80. As a result, inordinate heating of the individual optical fibers 82 within the primary bundle 80 is prevented.

Finally, it should be noted that the reflector unit 122 is preferably movable in the Z axis, and can be tilted as desired using conventional adjustment screws 129. Selective inward/outward rotation of the screws 129 alters the position of the reflector unit 122 so that the focal point thereof may be properly aligned with the light source 120. In addition, the light source 120 may optionally be connected to a conventional rheostatic voltage control unit 130 in order to selectively vary the intensity of the illuminating light delivered from the light source 120 to the primary bundle 80.

The probe 12 of the endoscope apparatus 10 further includes third light transmission means 139 within the medial portion 18 of the probe 12 for receiving visual images from the selected body cavity. In a preferred embodiment as illustrated in FIG. 1, the third light transmission means consists of a secondary bundle 140 of about 4000-6000 individual, elongate glass optical fibers 142. The individual optical fibers 142 within the secondary bundle 140 are commercially available from 3M Specialty Optical Fibers of West Haven, Conn. (U.S.A.). The secondary bundle 140 is substantially circular in cross-section, and fixedly positioned within the medial portion 18 of the probe 12 by placement of the secondary bundle 140 within a passageway 144 which extends entirely through the medial portion 18 of the probe 12 from the first end 14 to the second end 16. The secondary bundle 140 further includes a first end 146 and a second end 148, with the first end 146 being positioned adjacent the first end 14 of the probe 12 as shown in FIG. 1. In addition, the secondary bundle 140 has a preferred uniform diameter of about 250-500 microns with a preferred minimum bending radius of about 1.0 cm.

Preferably, the diameter of the secondary bundle 140 should be equal to or slightly greater than the diameter of the passageway 144 so that the secondary bundle 140 may be urged inwardly into the passageway 144 and fixedly retained therein through resilient frictional engagement between the secondary bundle 140 and the interior walls (not shown) of the passageway 144. Accordingly, in a preferred embodiment, the passageway 144 will have a uniform diameter of about 250– 500 microns. An adhesive (e.g. of the same general type described above which is used to secure the primary bundle 80 within the passageway 90) may also be used to additionally secure the secondary bundle 140 within the passageway 144.

Figure 5:
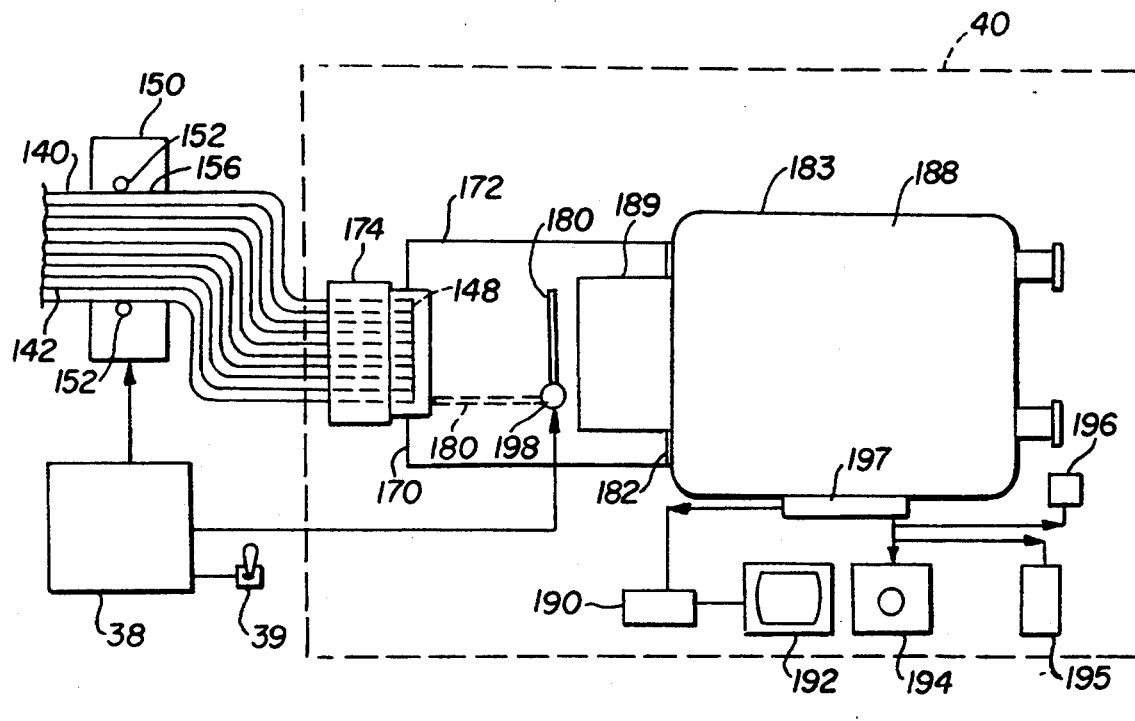
FIG. 5 is a schematic illustration of the observation means and associated components which are used with the probe of FIG. 1 to observe visual images from the selected body cavity.

In the alternative, the secondary bundle 140 may be movable within the passageway 144 in the same manner indicated above regarding optical fiber 21 by making the diameter of the passageway 144 slightly larger than the diameter of the secondary bundle 140 (e.g. so that there is a clearance between the secondary bundle 140 and the interior walls of the passageway 144 of about 25–50 microns). In this embodiment, movement of the secondary bundle 140 may be accomplished through the use of a conventional stepper motor unit 150 (FIG. 5) operatively connected to roller units 152 (e.g. made of rubber or the like) which frictionally communicate with portion 156 of the secondary bundle 140 adjacent the second end 148 thereof as illustrated in FIG. 5. Selective operation of the stepper motor unit 150 causes movement of the roller units 152 which correspondingly move the secondary bundle 140. The stepper motor unit 150 is preferably operated and controlled using microcomputer 38 and variable manual controller 39 as described above which are operatively connected to the stepper motor unit 150. It should also be noted that the stepper motor unit 150 and the roller units 152 may be of the same general type as the stepper motor unit 34 and roller units 35 indicated above. Furthermore, it is preferred that the secondary bundle 140 be coherent. The term "coherent" as used herein shall involve a situation in which the orientation of the fibers 142 (relative to each other) at the first end 146 of the secondary bundle 140 is the same as the orientation of the fibers 142 at the second end 148 of the bundle 140. The use of a coherent secondary bundle 140 is important because a coherent optical fiber bundle can normally transmit a visual image without the distortion or scrambling which typically occurs when a non-coherent bundle is used.

With reference to FIG. 1, the first end 146 of the secondary bundle 140 preferably includes a solid, transparent cap member in the form of a glass lens 160 affixed thereto using an adhesive composition known in the art (e.g. a material commercially sold under the name Lens Bond ™ by Summers Laboratories of Fort Washington, Pa. (U.S.A.)). The lens 160 is preferably of the gradient index variety sold under the name SELFOC® by NSG America of Somerset, N.J. (U.S.A.). This type of lens (which is well known in the art) is self-focusing, and does not require a spacer between the lens 160 and the image plane. The lens 160 is specifically designed to capture images from within the body cavity and focus such images onto the ends of the optical fibers 142 at the first end 146 of the secondary bundle 140. The lens 160 is preferably about 0.70–0.96 mm long, substantially the same diameter as the secondary bundle 140, and is coated with anti-reflective material (e.g. $MgF_2$). It is also important to note that the lens 160 should have an index of refraction substantially identical to that of the secondary bundle 140. Likewise, the adhesive material used to affix the lens 160 to the secondary bundle 140 should have an index of refraction substantially identical to that of the secondary bundle 140 and the lens 160. The proper matching of indices of refraction with respect to the foregoing items is desired in order to minimize light loss caused by reflectance at the interfaces and boundaries between dissimilar materials.

In a preferred embodiment wherein the secondary bundle 140 is fixedly secured within the passageway 144, the lens 160 and first end 146 of the secondary bundle 140 preferably extend slightly outward from the end face 32 of the first end 14 of probe 12. Furthermore, it should be noted that the outer surface 162 of the lens 160 has rounded edges 164 in order to ensure that tissues within the selected body cavity are not damaged during entry therein by the probe 12.

As shown in FIGS. 1 and 5, the second end 148 of the secondary bundle 140 extends outwardly from the second end 16 of the probe 12 and passes into the connection box 40 wherein it is operatively attached to wall 170 of a chamber 172 (shown schematically and in cross-section in FIG. 5) using a conventional connector unit 174 (e.g. a standard SMA connector or other comparable device). Within the chamber 172, a standard optical filter 180 is provided, the function of which will be described below. Operatively secured to and within wall 182 of the chamber 172 is observation means 183 (FIG. 1) which enables the visual images received from the secondary bundle 140 (e.g. the visual images generated by illuminating light within the body cavity supplied by the illuminating light source 120 and primary bundle 80) to be viewed by an operator of the endoscope apparatus 10. In a preferred embodiment, the observation means 183 will consist of a standard binocular operating microscope 188 which is designed to receive visual images from the second end 148 of the secondary bundle 140. An exemplary, commercially available binocular microscope suitable for use as the microscope 188 will involve a system manufactured by Zeiss, Inc. of Oberkochen, Germany, model no. OPMI-6. To use the microscope 188 in a most efficient manner, the microscope objective 189 is focused directly on the second end 148 of the secondary bundle 140. Proper and accurate alignment/coupling of the microscope objective 189 with respect to the second end 148 of the secondary bundle 140 is important in order to avoid any distortion of the images received by the microscope 188.

Use of the microscope 188 and associated components enables visual images from the selected body cavity to be viewed in a highly efficient and effective manner. In a preferred embodiment, the microscope 188 may be connected to an optional video camera assembly 190 (of the conventional CCD [charge coupled device] variety or the like) which is operatively connected to a variety of different accessories, including but not limited to a standard video monitor 192 as illustrated in FIG. 5. The video monitor 192 may also consist of a three dimensional video monitor which is viewable by the system operator without the use of any glasses which might normally be worn by the operator. In addition, the microscope 188 may optionally be connected to a conventional still camera 194 (e.g. preferably of the 35 mm variety), a conventional video printer unit 195, or a commercially available digital frame grabber/digital image archival system 196. Connection of the microscope 188 to the foregoing accessories may be accomplished using optical hardware which is known in the art, including but not limited to a standard beam-splitter assembly 197.

As indicated above, an optical filter 180 is provided which is pivotally mounted within the chamber 172 as illustrated in FIG. 5. During use of the microscope 188 and/or accessories associated therewith to view images from the selected body cavity, the optical filter 180 is raised to a substantially vertical position (either manually or through the use of microcomputer 38 which is operatively connected to a standard solenoid 198 attached to the optical filter 180). Raising the optical filter 180 to this position enables it to filter out potentially harmful laser light which could damage the eyes of the system operator/viewer as well as various optical components of the observation means 183. If the microcomputer 38 is used, the optical filter 180 would be raised automatically during operation of the laser light source 58.

The optical filter 180 is appropriately selected to filter out the particular laser light being generated by the laser light source 58. For example, if the laser light source 58 generates infra-red laser light, an infra-red optical filter 180 would be used. Thus, the optical filter 180 also acts as protection means in combination with and/or in addition to the mirror 52 (FIG. 3) which is used to interrupt the delivery of laser light from the laser light source 58 as described above. When the microscope 188 (and accessories associated therewith) is not in use, the optical filter 180 may be lowered to a substantially horizontal position as shown in phantom lines in FIG. 5 either manually or through the use of microcomputer 38 and solenoid 198. Accordingly, use of the microscope 188 (and video monitor 192, camera 194, video printer 195, and/or archival system 196) in association with the secondary bundle 140 of optical fibers 142 enables clear and distinct images to be viewed from within the selected body cavity.

Figure 2:
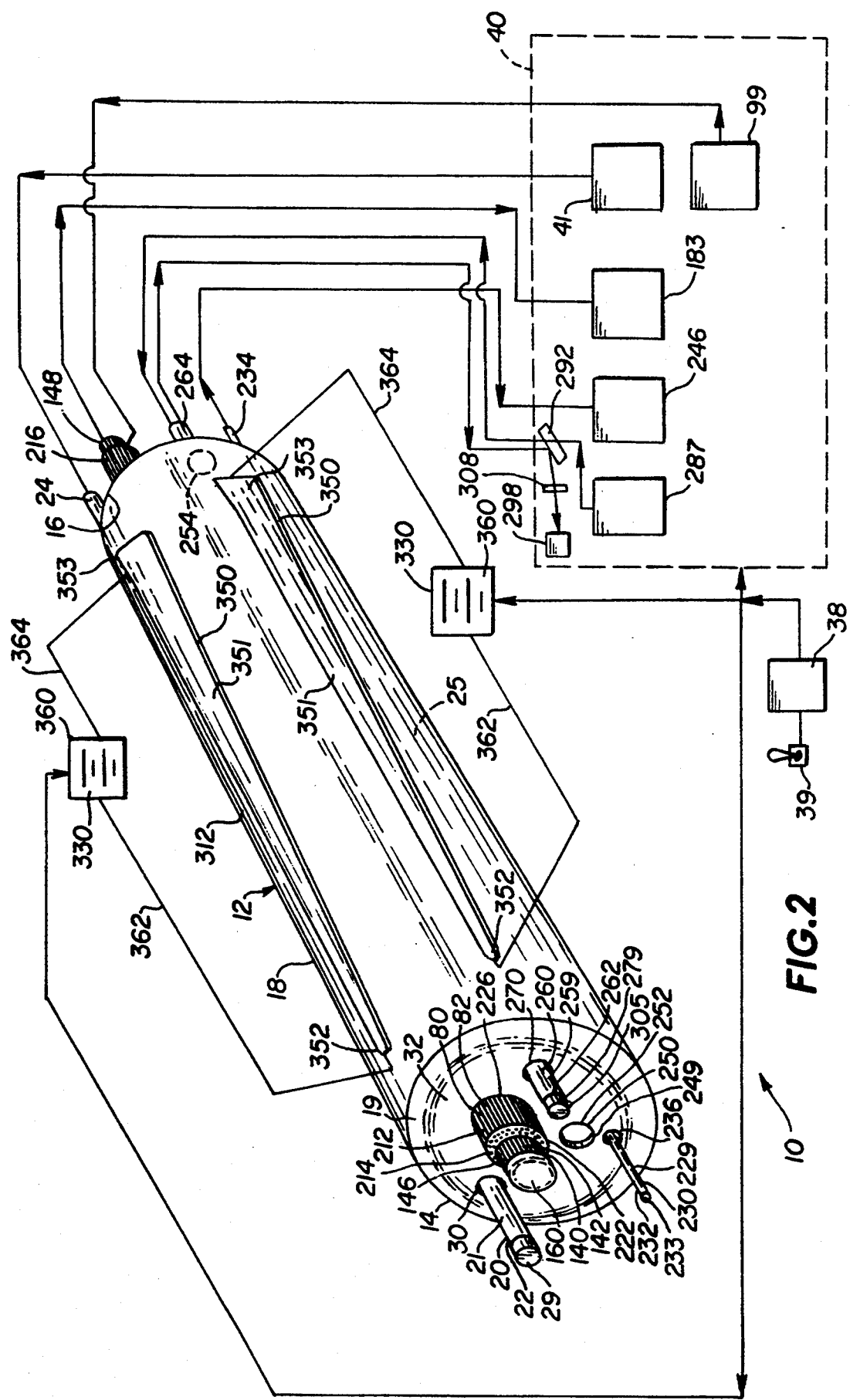
FIG. 2 is an enlarged front perspective view of an alternative embodiment of the endoscope probe of FIG. 1 wherein the probe is schematically illustrated.

An alternative embodiment of the probe 12 is illustrated in FIG. 2. All of the elements of the probe 12 in the embodiment of FIG. 2 are identical to those illustrated in FIG. 1 except where otherwise indicated. Specifically, with reference to FIG. 2, the secondary bundle 140 of optical fibers 142 is nested within (e.g. in the center of) the primary bundle 80 of optical fibers 82 as illustrated. In this configuration, the primary bundle 80 actually forms a ring structure 212 having a uniform ring thickness of about 20-50 microns with a first end 214 and a second end 216. Accordingly, the ring structure 212 and the secondary bundle 140 nested therein form a large tertiary optical bundle 222 within the medial portion 18 of the probe 12. The tertiary optical bundle 222 is preferably circular in cross-section, and has a uniform diameter of about 200-550 microns.

The tertiary optical bundle 222 is positioned within a passageway 226 through the medial portion 18 of the probe 12 which extends continuously from the first end 14 to the second end 16. Preferably, the diameter of the tertiary optical bundle 222 should be about equal to or slightly greater than the diameter of the passageway 226 so that the tertiary optical bundle 222 may be urged inwardly into the passageway 226 and fixedly retained therein through resilient frictional engagement between the tertiary optical bundle 222 and the interior walls (not shown) of the passageway 226. Accordingly, in a preferred embodiment, the passageway 226 will have a uniform diameter of about 190-540 microns. An adhesive (e.g. of the same general type described above which is used to secure primary bundle 80 within passageway 90) may additionally be used to secure the tertiary optical bundle 222 within the passageway 226. In the alternative, the tertiary optical bundle 222 may also be movable within the passageway 226 in the same manner described above regarding optical fiber 21 by making the diameter of the passageway 226 slightly larger than the diameter of the tertiary optical bundle 222 (e.g. so that there is a clearance between the tertiary optical bundle 222 and the interior walls of the passageway 226 of about 25-50 microns). Movement of the tertiary optical bundle 222 may then be accomplished through the use of a stepper motor/roller unit/computer system of exactly the same type described above relative to movement of the secondary bundle 140 as illustrated in FIG. 5.

In a preferred embodiment wherein the tertiary optical bundle 222 is fixedly secured within the passageway 226, the first end 214 of the ring structure 212 extends outwardly from the end face 32 of the first end 14 of the probe 12. The lens 160 and the first end 146 of the secondary bundle 140 preferably extend slightly outward from the first end 214 of the ring structure 212 as illustrated in FIG. 2. The second end 148 of the secondary bundle 140 is operatively attached to the observation means 183 and the associated components described above and illustrated in FIG. 5. The second end 216 of the ring structure 212 is operatively connected to the primary illumination means 99 and associated components described above with respect to primary bundle 80 as illustrated in FIG. 4.

The configuration of components described above and illustrated in FIG. 2 is primarily designed to produce a probe 12 with small dimensions. The remaining components used in the probe 12 of FIG. 2 (except as further indicated below) are substantially the same as those set forth in the embodiment of FIG. 1.

With reference to FIG. 1, the probe 12 further includes tissue potential sensing means 229 within the medial portion 18 of the probe 12 for receiving electrical potentials from tissue materials within the selected body cavity. Basically, with respect to the inner ear, a plurality of neurosensory hair cells are present therein. When specific sounds are applied in proximity to the ear, electrical cochlear potentials are generated by the hair cells in response to such sounds. For example, when sounds (e.g. clicks or tone bursts) are introduced into the ear, evoked potentials are generated in response to the sound stimulation in normal or pathogenic patterns. These potentials are measured by ECoG (as defined above), and include compound action potentials, cochlear microphonics, otoacoustic emissions (OAE) and summating potentials (SP). There are very specific abnormal pathological manifestations of ECoG waveforms which correlate with different disease etiologies or processes and their focal locations within the inner ear. The ability to directly identify, measure, and/or localize these pathologic manifestations and be able to correlate them with various inner ear abnormalities for the treatment thereof (e.g. using laser energy) is a significant advance in medical science.

In a preferred embodiment, the tissue potential sensing means 229 includes at least one and preferably about three elongate primary wire members 230, with each wire member 230 having a first end 232 and a second end 234. In a preferred embodiment, the first end 232 of each wire member 230 will include a spherical member or ball 233 which is fixedly secured to the first end 232 or formed as an integral part thereof. For the sake of clarity, only one primary wire member 230 is illustrated in FIG. 1. In addition, each of the primary wire members 230 has a preferred uniform diameter of about 5–10 microns. This size will enable electrical potentials to be measured down to single hair cells in the inner ear as described above. Each of the primary wire members 230 is preferably is made of platinum, silver, or a silver alloy (e.g. silver/silver chloride), and is selectively movable within the medial portion 18 of the probe 12. To enable such movement, each of the primary wire members 230 is positioned within a passageway 236 through the medial portion 18 of the probe 12 having a preferred diameter which is slightly larger than the diameter of the primary wire member 230 positioned therein. Each passageway 236 extends continuously from the first end 14 to the second end 16 of the probe 12 as illustrated. In a preferred embodiment, the diameter of each passageway 236 will be about 15–60 microns, thereby providing a clearance of about 10–55 microns between each primary wire member 230 and the interior walls of its associated passageway 236.

Figure 6:
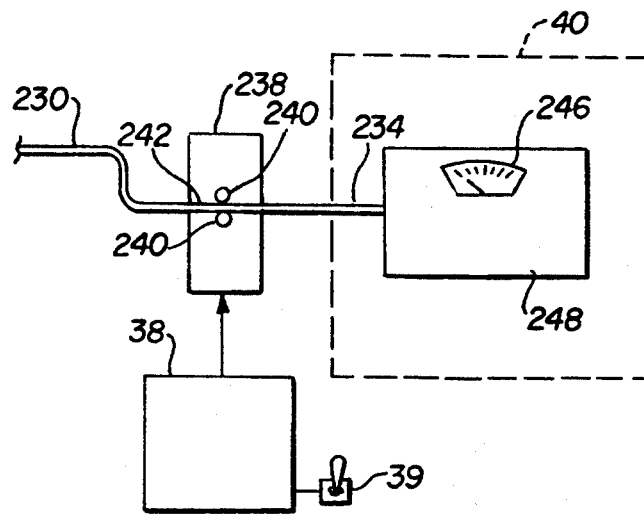
FIG. 6 is a schematic illustration of the detection means and associated components which are used with the probe of FIG. 1 to measure tissue electrical potentials in the selected body cavity.

As illustrated in FIG. 1, the first end 232 of each primary wire member 230 is generally positioned adjacent the first end 14 of the probe 12, and may be extended outwardly from the end face 32 by a preferred distance of about 1–10 mm to thereby touch tissue materials within the selected body cavity. In order to move each of the primary wire members 230, the second ends 234 of the primary wire members 230 (which extend outwardly beyond the second end 16 of the probe 12 as shown in FIG. 1) may be manipulated by the exertion of controlled force thereon. This manipulation is accomplished through the use of conventional stepper motor units 238 (FIG. 6), with each stepper motor unit 238 being operatively connected to a pair of roller units 240 (e.g. made of rubber or the like). Each pair of roller units 240 frictionally communicates with portion 242 of each primary wire member 230 as shown in FIG. 6. Selective operation of the stepper motor units 238 causes movement of the roller units 240 which correspondingly move the primary wire members 230 of the endoscope apparatus 10. The stepper motor units 238 are preferably operated and controlled using microcomputer 38 and variable manual controller 39 as described above which are operatively connected to the stepper motor units 238. It should also be noted that the stepper motor units 238 and the roller units 240 are of the same general type as the stepper motor unit 34 and roller units 35 described above.

Any electrical potentials received from the foregoing tissue materials are conducted through the primary wire members 230 and into detection means 246 (FIGS. 1 and 6) mounted externally from the probe 12 within the connection box 40. In a preferred embodiment as schematically illustrated in FIG. 6, the detection means 246 consists of a voltage amplifier/analog-to-digital-converter unit 248 which is monitored by microcomputer 38. An exemplary voltage amplifier/converter unit 248 is commercially available from Data Translation, Inc. of Marlboro, Mass. (U.S.A.)—(model number DT 2811). The voltage amplifier/converter unit 248 operates by first amplifying small electrical potentials/voltages received by the primary wire members 230, and then digitizing the electrical potentials/voltages using a device known as an analog-to-digital converter (hereinafter "ADC"), which is a conventional and widely available electronic component. In this manner, electrical potentials received from the primary wire members 230 may be quantified and analyzed in a highly accurate manner. In addition, it should also be noted that a commercially available ECoG detection system sold under the name "Viking II ™" by Nicolet, Inc. of Madison, Wis. (U.S.A.) may be used to interpret/analyze electrical potentials from the wire members 230.

With reference to FIG. 1, the probe 12 further includes fluid transmission means 249 therein so that various fluid materials (e.g. defined herein as liquids and/or gases) may be delivered to and from the selected body cavity. For example, it may be necessary and appropriate for liquid therapeutic agents and/or irrigating materials to be delivered to tissues within the selected body cavity. It may also be desirable or necessary for fluids within the body cavity to be removed/drained as desired (e.g. the removal of endolymph/perilymph samples from the inner ear for biochemical/immunological analysis). Furthermore, the fluid transmission means 249 may be used to remove/withdraw smoke or other vapors from within the selected body cavity which result from the use of laser surgical techniques. To accomplish this, the medial portion 18 of the probe 12 includes at least one and preferably two continuous passageways 250 therethrough. For the sake of clarity, only one passageway 250 is illustrated in FIG. 1. Passageway 250 extends entirely through the medial portion 18 as illustrated in FIG. 1 from the first end 14 of the probe 12 to the second end 16. Each passageway 250 will have a substantially uniform diameter which is preferably about 100–200 microns. Likewise, each passageway 250 will have a first end 252 which is positioned at the first end 14 of the probe 12 and a second end 254 which is positioned at the second end 16 of the probe 12. Using the passageways 250, the transfer/drainage of materials from the body cavity is readily accomplished through the medial portion 18 of the probe 12 as previously indicated. More specifically, the application of negative pressure to the passageways 250 will enable fluids or tissue/cellular materials to be removed from the body cavity, while the exertion of positive pressure through the passageways 250 will allow fluids and the like to be delivered to various points within the body cavity.

Figure 7:
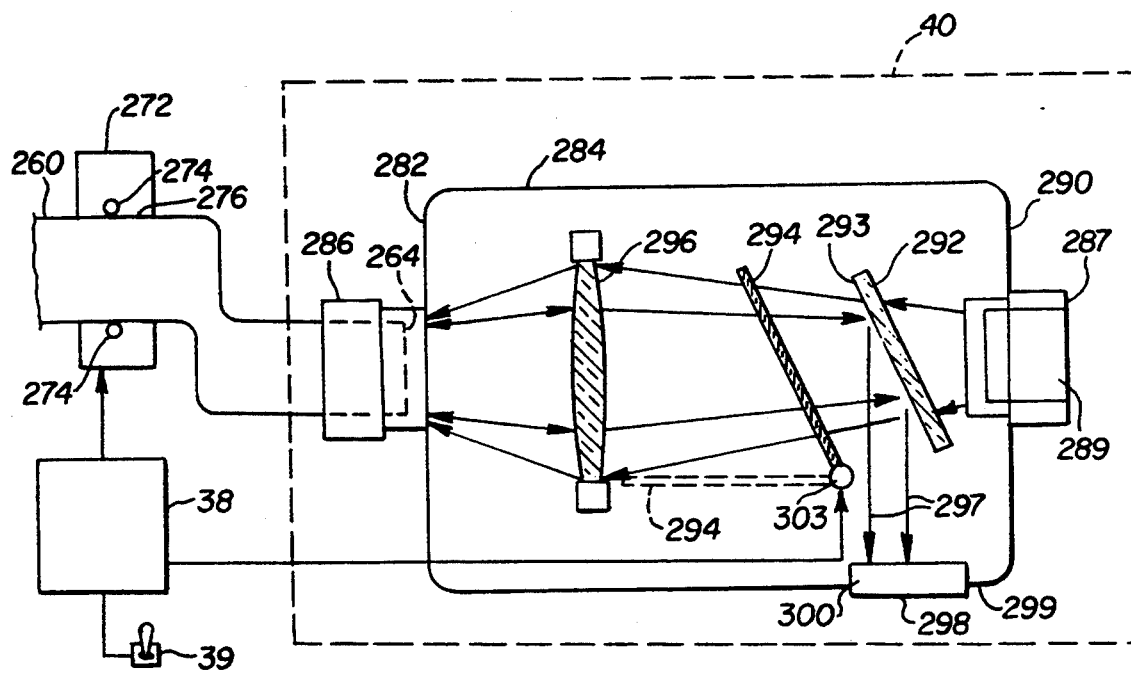
FIG. 7 is a schematic illustration of the monitoring means, secondary illuminating means, and associated components which are used with the probe of FIG. 1 to detect fluid pressure and temperature levels within the selected body cavity.

Next, the probe 12 of the endoscope apparatus 10 includes a unique subsystem for making accurate temperature and fluid pressure measurements from within a selected body cavity. Specifically, the probe 12 includes fourth light transmission means 259 which is used to make fluid pressure and temperature measurements within the selected body cavity in a highly unique and effective manner. Specifically, the fourth light transmission means 259 consists of a secondary elongate optical fiber 260 which is movably positioned within the medial portion 18 of the probe 12. The optical fiber 260 consists of a conventional glass fiber which may be commercially obtained from 3M Specialty Optical Fibers of West Haven, Conn. (U.S.A.). The optical fiber 260 has a uniform diameter of about 50–100 microns, and includes a first end 262 and a second end 264 as illustrated in FIG. 1. The first end 262 of the optical fiber 260 is generally positioned adjacent the first end 14 of the probe 12. Furthermore, in a preferred embodiment, the first end 262 of the optical fiber 260 is movable outwardly by a distance of about 1–10 mm from the end face 32 of the first end 14 of probe 12. This is accomplished through placement of the optical fiber 260 within a passageway 270 having a diameter which is slightly larger than that of the optical fiber 260 so that the optical fiber 260 may freely move therein. The passageway 270 extends continuously within the medial portion 18 of the probe 12 from the first end 14 to the second end 16 thereof. Preferably, the passageway 270 has a uniform diameter of about 100–150 microns, thereby providing a preferred clearance between the optical fiber 260 and the interior walls (not shown) of the passageway 270 of about 50 microns. In addition, movement of the optical fiber 260 within the passageway 270 may take place through the use of a conventional stepper motor unit 272 (FIG. 7) operatively connected to roller units 274 (e.g. made of rubber or the like) which frictionally communicate with portion 276 of the optical fiber 260 as illustrated in FIG. 7. Selective operation of the stepper motor unit 272 causes movement of the roller units 274 which correspondingly move the optical fiber 260. The stepper motor unit 272 is preferably operated and controlled using microcomputer 38 and variable manual controller 39 as described above which are operatively connected to the stepper motor unit 272. It should also be noted that the stepper motor unit 272 and the roller units 274 are of the same general type as the stepper motor unit 34 and roller units 35 described above.

In order to make pressure and temperature measurements using the optical fiber 260, the first end 262 thereof is uniquely configured to include sensing means 279 preferably in the form of at least one liquid crystal 280 thereon which is adhered to the first end 262 by conventional photopolymerization processes, or through the use of a known optical epoxy composition (e.g. a product sold under the name Lens Bond ™ by Summers Laboratories of Fort Washington, Pa. (U.S.A.)). The liquid crystal 280 is of a type wherein the light reflectivity of the crystal 280 will vary, depending on the temperature, fluid pressure, and (to a minor extent) pH conditions to which it is exposed. A exemplary liquid crystal 280 suitable for use herein is commercially available from Sensor Kinetics, Inc. of Newark, N.J. (U.S.A.). It basically consists of a supply of micron-sized crystals dispersed within a polymer matrix whose reflective properties change as their orientation changes.

As indicated above, the light reflectivity of the liquid crystal 280 will vary, depending primarily on temperature and fluid pressure conditions within the selected body cavity. These characteristics are especially useful in determining the environmental conditions within the selected body cavity (e.g. the inner ear). To accomplish this goal in accordance with a preferred embodiment of the present invention as shown in FIGS. 1 and 7, the second end 264 of the optical fiber 260 is operatively connected to wall 282 of a chamber 284 (shown schematically and in cross-section in FIG. 7) using a conventional connector unit 286 (e.g. a standard SMA connector or the like). Additional light from a secondary illumination means 287 is then directed into the second end 264 of the optical fiber 260. In a preferred embodiment, the secondary illumination means 287 will consist of a light delivery unit 289 (e.g. a halogen or Xe light source commercially available from ILC Technology, Inc. of Sunnyvale, Calif. (U.S.A.) which is fixedly mounted to and within wall 290 of the chamber 284 as illustrated in FIG. 7. Light from the light delivery unit 289 thereafter passes through a one-way mirror 292 having a reflective surface 293. The one-way mirror 292 is preferably constructed of glass or quartz, with the reflective surface 293 being manufactured of aluminum, silver, or gold. An exemplary mirror 292 suitable for use in accordance with the present invention is commercially available from Melles Griot, Inc. of Irvine, Calif. (U.S.A.).

After passing through the one-way mirror 292, light from the delivery unit 289 thereafter passes through a filter 294 (described below) and enters a lens 296 which, in a preferred embodiment may involve an aspheric or a fiber coupling sphere configuration known in the art which is preferably coated with a conventional anti-reflective material (e.g. $MgF_2$). In order to be effective, it is preferred that the lens 296 be movable along the X, Y, and Z axes. Likewise, the F# of the lens 296 is equal to $\frac{1}{2}$(NA) wherein NA is as defined above with respect to lens 50.

Next, after passing through the lens 296, light from the delivery unit 289 enters the second end 264 of the optical fiber 260 and travels therethrough until it reaches the first end 262 and the liquid crystal 280 secured to the first end 262. The light will then strike the liquid crystal 280 and be partially reflected back into and through the optical fiber 260. As noted above, the amount of reflected light will primarily depend on the temperature, fluid pressure, and (to a minor extent) pH characteristics of the body cavity in which the liquid crystal 280 is positioned. The reflected light passes back through the optical fiber 260, through the lens 296 and through the filter 294. Thereafter, it strikes the reflective surface 293 of the one-way mirror 292. Because the one-way mirror 292 is positioned at a downwardly-sloped angle of approximately a 45° as illustrated in FIG. 7, reflected light coming from the optical fiber 260 which strikes the surface 293 of the one-way mirror 292 is directed downwardly in the direction of arrows 297 toward and into monitoring means 298 (FIGS. 1 and 7) within the connection box 40. The monitoring means 298 is operatively attached to and within wall 299 of the chamber 284 as schematically shown in FIG. 7. In a preferred embodiment, the monitoring means 298 will consist of a standard spectrophotometer 300 (e.g. a linear array photodiode coupled to a spectrometer) which is again secured to and within wall 299 of the chamber 284. An exemplary commercial spectrophotometer 300 suitable for the purposes set forth herein would include an apparatus sold under the name Quikscan ™ by Spex Industries, Inc. of Edison, N.J. (U.S.A.). The spectrophotometer 300 is designed to read the amount of light reflected from the liquid crystal 280. Accordingly, the amount of reflected light may thereafter by used to determine fluid pressure and temperature levels within the selected body cavity. This goal is facilitated using the movement capabilities of the optical fiber 260 wherein the first end 262 of the optical fiber 260 and liquid crystal 280 attached thereto may be moved outwardly from the probe 12 within the body cavity so that the liquid crystal 280 actually touches tissue and/or fluid materials therein.

In order to use the foregoing components to individually measure temperature and fluid pressure levels within a body cavity, each of these physical parameters can be determined independently of each other by monitoring the change in reflectance at two or more different wavelengths. The reflectivity at each wavelength will change by the same percentage in response to fluid pressure changes within the selected body cavity. However, the reflectivity at each wavelength changes by different percentages in response to fluid temperature changes within the body cavity. Accordingly, calibration of the liquid crystal 280 in environments of differing pressure and temperature will enable independent and absolute measurements of these parameters to be achieved.

As further illustrated in FIG. 7 and mentioned above, chamber 284 also includes a movable optical filter 294 of conventional design which is positioned between the lens 296 and the one-way mirror 292. The optical filter 294 is designed to filter out any laser light which may pass through liquid crystal 280 and optical fiber 260 during operation of the laser light source 58. The passage of such laser light is undesirable in that it will typically interfere with proper operation of the spectrophotometer 300, thereby causing inaccurate readings to be obtained. To prevent this from occurring, the optical filter 294 is raised to at least about a 45° angle as shown in FIG. 7 in order to block the passage of any laser light into the one-way mirror 292 and the spectrophotometer 300. In a preferred embodiment, the optical filter 294 will be interchangeable with respect to the laser light wavelength being used. For example, if an infra-red laser light source 58 is used in the endoscope apparatus 10, an infra-red optical filter 294 would be appropriate.

When the laser light source 58 is not in operation and laser light is not passing through the optical fiber 260, the filter 294 may then be lowered to a substantially horizontal position as illustrated in FIG. 7 in phantom lines. Movement of the optical filter 294 as described herein may be accomplished manually or preferably through the use of a conventional solenoid unit 303 or the like which is attached to the optical filter 294 and operatively connected to microcomputer 38. Using these components, the microcomputer 38 will determine when the laser light source 58 is operating and automatically raise the optical filter 294 to the position shown in FIG. 7.

In an alternative embodiment of the probe 12 as shown in FIG. 2, a different type of sensing means 279 will be used. Specifically, the first end 262 of the optical fiber will have a fluorescent coating 305 applied thereto (e.g. photopolymerized thereon). An exemplary and suitable material for this purpose will include but not be limited to N-fluoresceinylacrylamide which is commercially available from the Sigma Chemical Co. of St. Louis, Mo. (U.S.A.). In this embodiment, light applied to the coating 305 will cause it to fluoresce, with the magnitude and spectrum of the fluorescence being dependent on temperature, fluid pressure, and (to a minor extent) pH conditions within the selected body cavity. The remaining portions of the present invention which are used in connection with the fluorescent coating 305 are identical to those listed above relative to the liquid crystal detection system (except as indicated below). To measure temperature and fluid pressure levels within the selected body cavity, light is initially provided from the light delivery unit 289 which, in this embodiment, will preferably consist of a conventional laser light source (e.g. an argon laser designed to deliver light having a wavelength of 488 nm). Such a laser light source is commercially available from a number of manufacturers, including but not limited to Spectra-Physics Lasers, Inc. of Mountain View, Calif. (U.S.A.). Thereafter, light from the delivery unit 289 passes through the one-way mirror 292, filter 294, and lens 296. Next, after passing through the lens 296, the light enters the second end 264 of the optical fiber 260 and travels through the fiber 260 until it reaches the first end 262 and the fluorescent coating 305 thereon. The light will then strike the coating 305, causing it to produce fluorescent light. The fluorescent light will then pass back into and through the optical fiber 260. As noted above, the magnitude/spectrum of the fluorescent light will depend primarily on the temperature and fluid pressure characteristics of the body cavity in which the coating 305 is positioned as described in greater detail below. After travelling through the optical fiber 260, the fluorescent light passes through the lens 296 and filter 294. Thereafter, it strikes the reflective surface 293 of the one-way mirror 292. Because the one-way mirror 292 is positioned at approximately a 45° angle as illustrated in FIG. 7, fluorescent light coming from the optical fiber 260 which strikes the surface 293 of the one-way mirror 292 is directed downwardly in the direction of arrows 297, preferably toward and through a fluorescent filter 308 shown in FIG. 2 (e.g. a long pass or band pass fluorescent filter which is well known in the art and capable of transmitting light having a wavelength greater than the light used to activate the fluorescent coating 305). Thereafter, the filtered light passes into the monitoring means 298 (FIGS. 2 and 7) within the connection box 40 which consists of the spectrophotometer 300. The spectrophotometer 300 is designed to read the amount and spectrum of fluorescent light generated by the coating 305, with the amount/spectrum of such light being usable to determine fluid pressure and temperature levels within the selected body cavity. This goal is again facilitated using the movement capabilities of the optical fiber 260 wherein the first end 262 of the optical fiber 260 and fluorescent coating 305 thereon may be moved outwardly within the body cavity so that the coating 305 actually touches tissue and/or fluid materials therein.

In order to use the foregoing components to individually measure temperature and fluid pressure levels within a body cavity, each of these physical parameters can be determined independently of each other. This is accomplished in the same manner set forth above relative to the liquid crystal 280.

Finally, it is highly important for the probe 12 of the endoscope apparatus 10 to be movable within the selected body cavity. The motion capabilities of the probe 12 must be accurately controllable in order to prevent damage to tissue materials within the body cavity (e.g. rupture from one body cavity to another), and to enable precise observations/measurements to be made therein. To accomplish this goal in a highly efficient manner, steering means 309 (FIG. 1) is provided within the medial portion 18 of the probe 12 which enables the manipulation thereof in an accurate and careful manner within the selected body cavity. Specifically, the steering means 309 preferably consists of a plurality of secondary wire members 310 (at least two and preferably four) which extend longitudinally through the medial portion 18 of the probe 12 as illustrated in FIG. 1. In the embodiment of FIG. 1, four secondary wire members 310 are used which are spaced equidistantly from each other directly beneath the outer surface 312 of the probe 12 as illustrated. In a preferred embodiment, each secondary wire member 310 is manufactured of a resilient, substantially inert metal (e.g. stainless steel), and has a uniform diameter of about 20–50 microns.

Each of the secondary wire members 310 includes a first end 313 and a second end 314. In a preferred embodiment, the first end 313 of each secondary wire member 310 is secured to the medial portion 18 of the probe 12 at the first end 14 thereof as further described below. The second end 314 of each secondary wire member 310 extends outwardly from the second end 16 of the probe 12.

In a preferred embodiment, each secondary wire member 310 is positioned within a passageway 320 which extends entirely through the medial portion 18 of the probe 12 from the first end 14 to the second end 16. A representative passageway 320 extending through the medial portion 18 is partially illustrated in FIG. 1 in dashed lines. Although only one passageway 320 is shown in FIG. 1 for the sake of clarity, each secondary wire member 310 is positioned within an individual passageway 320 as noted above.

Each passageway 320 is preferably designed to have a diameter which is slightly larger than the diameter of the secondary wire member 310 positioned therein. Specifically, each passageway 320 will preferably have a diameter of about 30–70 microns, thereby providing a clearance of about 10–20 microns between the inner walls (not shown) of the passageway 320 and the secondary wire member 310 positioned therein. However, so that the secondary wire members 310 may be used to steer the probe 12, the first end 313 of each secondary wire member 310 is fixedly secured to the first end 14 of the probe 12. To accomplish this in accordance with a preferred embodiment of the present invention, the first end 313 of each secondary wire member 310 is preferably configured to include a substantially circular head portion 329. The head portion 329 of each secondary wire member 310 will have a diameter which exceeds the diameter of the passageway 320 associated with the wire member 310 under consideration. To secure the first end 313 of each secondary wire member 310 to the first end 14 of the probe 12, a portion of adhesive material (e.g. a conventional epoxy adhesive) is applied to the head portion 329 of each wire member 310. Thereafter, the head portion 329 of each wire member 310 is positioned against the end face 32 (FIG. 1) of the probe 12. In this manner, the head portion 329 (and first end 313) of each secondary wire member 310 may be secured to the first end 14 of the probe 12. The remaining portions of each secondary wire member 310 (other than the first end 313 and head portion 329 thereof) will be free to move and flex within its associated passageway 320. This design facilitates movement and control of the entire probe 12 using the secondary wire members 310 as described below.

Figure 8:
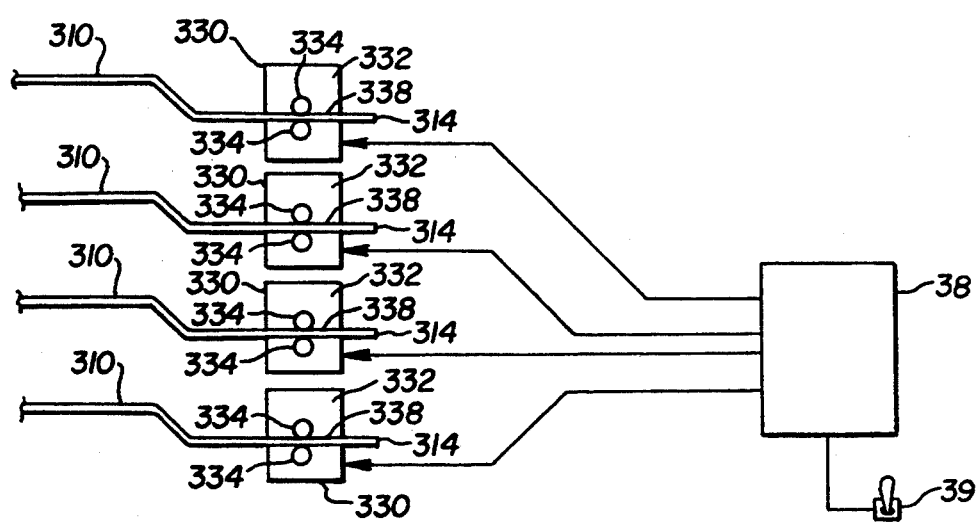
FIG. 8 is a schematic illustration of the manipulator means and associated components which are used with the probe of FIG. 1 to move/steer the probe and adjust the position thereof within the selected body cavity.

The exertion of force on the second end 314 of each secondary wire member 310 (either pushing, pulling, or rotational force) will cause corresponding movement of the entire probe 12. Accordingly, selective movement of the secondary wire members 310 in the probe 12 will enable the probe 12 to be accurately moved in a variety of different directions. With reference to FIGS. 1 and 8, manipulator means 330 is provided in order to selectively move some or all of the secondary wire members 310 within the probe 12. In a preferred embodiment, the manipulator means 330 consists of a conventional stepper motor unit 332 associated with each secondary wire member 310, with each stepper motor unit 332 being operatively connected to a pair of roller units 334 (e.g. made of rubber or the like) as shown in FIG. 8. Each pair of roller units frictionally communicates with portion 338 of each secondary wire member 310 in order to produce a preferred movement ratio of about 30:1 to 200:1.

Selective operation of the stepper motor units 332 causes movement of the roller units 334 which correspondingly move the secondary wire members 310. The stepper motor units 332 are preferably operated and controlled using microcomputer 38 and variable manual controller 39 as described above which are operatively connected to the stepper motor units 332 as illustrated in FIG. 8. It should also be noted that the stepper motor units 332 and the roller units 334 are of the same general type as the stepper motor unit 34 and roller units 35 described above. Accordingly, using the foregoing arrangement of components, movement of the probe 12 may be accomplished in a highly accurate and precise manner within the selected body cavity.

Finally, an alternative steering system for the probe 12 is illustrated in FIG. 2. This alternative steering system involves a plurality of elongate bands 350 of piezoelectric crystal material deposited longitudinally on the outer surface 312 of the probe 12. Deposition of the bands 350 may be accomplished by processes known in the art including but not limited to atomic sputtering, photolithography, or adhesion of the selected piezoelectric material to the outer surface 312 of the probe using a conventional adhesive (e.g. epoxy adhesive materials). In a preferred embodiment, four bands 350 will be used, with such bands 350 being spaced equidistantly from each other. Piezoelectric materials basically involve chemical compositions which generate internal stress forces upon the application of electricity thereto. As a result, the application of an appropriate electrical voltage causes physical movement of the piezoelectric materials. Examples of preferred piezoelectric materials suitable for use in forming the bands 350 include but are not limited to $BaTiO_3$, as well as other comparable piezoelectric materials known in the art. Likewise, in a preferred embodiment, each band 350 will have a uniform thickness of about 10–25 microns, and will extend continuously from the first end 14 to the second end 16 of the probe 12 along the outer surface 312 thereof. Furthermore, it is preferred that each band 350 be coated with a layer 351 of a non-conductive compound (e.g. rubber) which functions as an external insulator.

With continued reference to FIG. 2, each band 350 has a first end 352 (adjacent first end 14 of the probe 12) and a second end 353 (adjacent second end 16 of the probe 12). As shown in FIG. 2, the preferred width of each band 350 will gradually increase from the first end 352 to the second end 353. For example, the preferred width of each band 350 at first end 352 will be about 20–200 microns while the width of the band 350 at the second end 353 will be about 100–400 microns. The greater width of each band 350 at the second end 353 thereof is desirable in order to provide the probe 12 with more bending capability at the first end 14 thereof. Enhanced bending capability at the first end 14 enables the first end 14 to more readily pass through small curves and passageways which may be encountered during use of the probe 12 in a selected body cavity.

In order to cause movement and manipulation of the probe 12 using the steering system illustrated in FIG. 2, each band 350 is electrically connected to a separate variable electrical power supply unit 360 of conventional construction which is operatively connected to the first end 352 of each band 350 using a conductive lead 362. Likewise, each power supply unit 360 is operatively connected to the second end 353 of each band 350 using a conductive lead 364. Accordingly, in this embodiment, the power supply units 360 are being used as manipulator means 330 with respect to the bands 350 and probe 12. The selected application of electricity from the power supply unit 360 (e.g. about 0.1–10 V) to each band 350 will cause the bending of such band 350, thereby causing the entire probe 12 to move. The operation of all bands 350 and power supply units 360 associated with the probe 12 may be coordinated through operative connection of the individual power supply units 360 with microcomputer 38 and variable manual controller 39. The use of these components in association with the power supply units 360 and bands 350 enables the accurate manipulation of the probe 12 within the selected body cavity.

Finally, manipulation of the probe 12 within the body cavity is facilitated through the use of an optional zone 369 of a plurality of accordion-like annular segments or folds 370 which are integrally formed within the exterior surface 312 of the probe 12 as illustrated in FIG. 1. The zone 369 may include a variable number of folds 370, although it is preferred that between about 2–10 folds 370 be used. Furthermore, it is preferred that the zone 369 of folds 370 be positioned adjacent the first end 14 of the probe 12 as illustrated. Use of the folds 370 increases the flexibility of the probe 12 at the first end 14 thereof, and more readily enables the first end 14 of the probe 12 to be selectively moved and/or manipulated by the steering means 309.

The present invention as described above represents an advanced endoscope apparatus which is capable of performing multiple functions within a selected body cavity. Not only does the invention facilitate diagnostic tissue/fluid analysis within the body cavity, but it also enables the effective delivery of laser light and/or liquid therapeutic agents to the body cavity, as well as the measurement of electrical potentials within body cavity tissues. Thus, the invention represents a substantial advance in medical instrument technology. Having herein described preferred embodiments of the present invention, it is anticipated that suitable modifications may be made thereto by individuals skilled in the art within the scope of the invention. For example, variations in construction materials, dimensions, and arrangements of components may be made to the endoscope apparatus described herein which remain within the scope of the invention. Also, the invention may be used in a variety of different physiological environments. Thus, the invention shall only be construed in accordance with the following claims:

The invention that is claimed is:

1. An endoscope apparatus for use in analyzing, treating, and diagnosing conditions within a body cavity comprising:

a flexible probe having a medial portion, a first end, and a second end, said first end of said probe being sized for placement within said body cavity;

laser light supply means operatively connected to said probe for delivering laser light to said probe;

first light transmission means positioned within said medial portion of said probe for receiving said laser light from said laser light supply means, said first light transmission means being operatively connected to said laser light supply means in order to receive said laser light therefrom, said laser light being delivered by said first light transmission means to said body cavity when said first end of said probe is positioned therein;

primary illumination means operatively connected to said probe for delivering illuminating light thereto;

second light transmission means positioned within said medial portion of said probe for receiving said illuminating light from said primary illumination means, said second light transmission means being operatively connected to said primary illumination means in order to receive said illuminating light therefrom, said illuminating light being delivered by said second light transmission means to said body cavity when said first end of said probe is positioned therein;

third light transmission means positioned within said medial portion of said probe for receiving visual images from said body cavity, said visual images being generated by said illuminating light delivered from said second light transmission means into said body cavity;

observation means operatively connected to said third light transmission means for enabling said visual images received from said third light transmission means to be viewed by an operator of said endoscope apparatus;

secondary illumination means operatively connected to said probe for delivering additional light thereto;

fourth light transmission means positioned within said medial portion of said probe and operatively connected to said secondary illumination means for receiving said additional light from said secondary illumination means;

temperature and fluid pressure sensing means operatively connected to said fourth light transmission means for determining temperature and fluid pressure levels within said body cavity;

tissue potential sensing means positioned within said medial portion of said probe for receiving electrical potentials from tissue materials within said body cavity, said tissue potential sensing means comprising at least one elongate electrically conductive metallic primary wire member positioned within said medial portion of said probe, with at least a portion of said primary wire member extending outwardly from said first end of said probe, said portion of said primary wire member being exposed so that said portion of said primary wire member can directly contact tissue materials; and detection means for detecting and analyzing said electrical potentials from said tissue materials within said body cavity, said detection means being operatively connected to said tissue potential sensing means.

2. The endoscope apparatus of claim 1 wherein said fourth light transmission means comprises at least one elongate optical fiber positioned within said medial portion of said probe, said optical fiber comprising a first end and a second end, and said temperature and fluid pressure sensing means comprises at least one liquid crystal secured to said first end of said optical fiber, said second end of said optical fiber being operatively connected to said secondary illumination means so that said optical fiber may receive said additional light from said secondary illumination means, said additional light passing through said optical fiber and striking said liquid crystal, said liquid crystal thereafter reflecting at least a portion of said additional light back through said optical fiber toward said second end thereof in an amount dependent on temperature and fluid pressure levels within said body cavity, said endoscope apparatus further comprising monitoring means operatively connected to said second end of said optical fiber for detecting and analyzing said portion of said additional light which is reflected back through said optical fiber by said liquid crystal.

3. The endoscope apparatus of claim 1 wherein said fourth light transmission means comprises at least one elongate optical fiber positioned within said medial portion of said probe, said optical fiber comprising a first end and a second end, and said temperature and fluid pressure sensing means comprises a portion of fluorescent material affixed to said first end of said optical fiber, said second end of said optical fiber being operatively connected to said secondary illumination means so that said optical fiber may receive said additional light from said secondary illumination means, said additional light passing through said optical fiber and striking said portion of fluorescent material, said portion of fluorescent material thereafter generating fluorescent light in response to said additional light coming in contact therewith, said fluorescent light being generated in an amount dependent on temperature and fluid pressure levels within said body cavity, said fluorescent light travelling back through said optical fiber toward said second end thereof, said endoscope apparatus further comprising monitoring means operatively connected to said second end of said optical fiber for detecting and analyzing said fluorescent light which travels back through said optical fiber.

4. The endoscope apparatus of claim 1 further comprising steering means positioned within said medial portion of said probe for manipulating and moving said probe within said body cavity, said steering means comprising a plurality of elongate secondary wire members positioned within said medial portion of said probe, each of said secondary wire members being secured to said probe at said first end of said probe, whereby exertion of force on any of said elongate secondary wire members causes movement of said probe.

5. The endoscope apparatus of claim 4 further comprising manipulator means for selectively exerting force on each of said elongate secondary wire members in order to manipulate and move said probe within said body cavity.

6. The endoscope apparatus of claim 1 wherein said observation means comprises a binocular microscope.

7. The endoscope apparatus of claim 1 further comprising protection means for preventing passage of any of said laser light from said laser light supply means into said observation means when said laser light supply means is in operation, said protection means comprising a pivotally movable mirror member positioned in front of said laser light supply means, said mirror member being oriented in a horizontal position when blockage of laser light from said laser light supply means is not desired and oriented in an upwardly tilted position when blockage of laser light from said laser light supply means is desired.

8. An endoscope apparatus for use in analyzing, treating, and diagnosing conditions within a body cavity comprising:

a flexible probe having a medial portion, a first end, and a second end, said first end of said probe being sized for placement within said body cavity;

laser light supply means operatively connected to said probe for delivering laser light thereto;

first light transmission means positioned within said medial portion of said probe for receiving said laser light from said laser light supply means, said first light transmission means comprising at least one elongate primary optical fiber positioned within said medial portion of said probe, said primary optical fiber being operatively connected to said laser light supply means in order to receive said laser light therefrom, said laser light being delivered by said first light transmission means to said body cavity when said first end of said probe is positioned therein;

primary illumination means operatively connected to said probe for delivering illuminating light thereto;

second light transmission means positioned within said medial portion of said probe for receiving said illuminating light from said primary illumination means, said second light transmission means comprising a primary bundle of individual elongate optical fibers, said primary bundle being operatively connected to said primary illumination means in order to receive said illuminating light therefrom, said illuminating light being delivered by said second light transmission means to said body cavity when said first end of said probe is positioned therein;

third light transmission means positioned within said medial portion of said probe for receiving visual images from said body cavity, said visual images being generated by said illuminating light delivered from said second light transmission means into said body cavity, said third light transmission means comprising a secondary bundle of individual elongate optical fibers, said secondary bundle comprising a first end and a second end, said first end of said secondary bundle comprising a transparent cap member secured thereto, said transparent cap member functioning as a lens for directing said illuminating light into said secondary bundle from said body cavity;

observation means operatively connected to said third light transmission means for enabling said visual images received from said third light transmission means to be viewed by an operator of said endoscope apparatus;

protection means for preventing passage of any of said laser light from said laser light supply means into said observation means when said laser light supply means is in operation, said protection means comprising a pivotally movable mirror member positioned in front of said laser light supply means, said mirror member being oriented in a horizontal position when blockage of laser light from said laser light supply means is not desired and oriented in an upwardly tilted position when blockage of laser light from said laser light supply means is desired;

secondary illumination means operatively connected to said probe for delivering additional light thereto;

fourth light transmission means positioned within said medial portion of said probe for receiving said additional light from said secondary illumination means, said fourth light transmission means comprising at least one elongate secondary optical fiber positioned within said medial portion of said probe, said secondary optical fiber comprising a first end and a second end, said second end of said secondary optical fiber being operatively connected to said secondary illumination means;

temperature and fluid pressure sensing means operatively connected to said fourth light transmission means for determining temperature and fluid pressure levels within said body cavity;

fluid transmission means within said medial portion of said probe for delivering fluid materials to and from said body cavity through said probe, said fluid transmission means comprising at least one continuous passageway through said probe from said first end of said probe to said second end of said probe;

tissue potential sensing means positioned within said medial portion of said probe for receiving electrical potentials from tissue materials within said body cavity, said tissue potential sensing means comprising at least one elongate electrically conductive metallic primary wire member positioned within said medial portion of said probe, with at least a portion of said primary wire member extending outwardly from said first end of said probe, said portion of said primary wire member being exposed so that said portion of said primary wire member can directly contact tissue materials;

detection means for detecting and analyzing said electrical potentials from said tissue materials within said body cavity, said detection means being operatively connected to said tissue potential sensing means;

steering means positioned within said medial portion of said probe for manipulating and moving said probe within said body cavity, said steering means comprising a plurality of elongate secondary wire members positioned within said medial portion of said probe, each of said secondary wire members being secured to said probe at said first end of said probe, whereby exertion of force on any of said secondary wire members causes movement of said probe; and manipulator means for selectively exerting force on each of said elongate secondary wire members in order to manipulate and move said probe within said body cavity.

9. The endoscope apparatus of claim 8 wherein said temperature and fluid pressure sensing means comprises:

at least one liquid crystal secured to said first end of said secondary optical fiber, said additional light from said secondary illumination means passing through said secondary optical fiber and striking said liquid crystal, said liquid crystal thereafter reflecting at least a portion of said additional light back through said secondary optical fiber toward said second end of said secondary optical fiber in an amount dependent on temperature and fluid pressure levels within said body cavity, said endoscope apparatus further comprising monitoring means operatively connected to said second end of said secondary optical fiber for detecting and analyzing said portion of said additional light which is reflected back through said secondary optical fiber by said liquid crystal.

10. The endoscope apparatus of claim 8 wherein said temperature and fluid pressure sensing means comprises:

a portion of fluorescent material affixed to said first end of said secondary optical fiber, said additional light from said secondary illumination means passing through said secondary optical fiber and striking said portion of fluorescent material, said portion of fluorescent material thereafter generating fluorescent light in response to said additional light coming in contact therewith, said fluorescent light being generated in an amount dependent on temperature and fluid pressure levels within said body cavity, said fluorescent light travelling back through said secondary optical fiber toward said second end of said secondary optical fiber, said endoscope apparatus further comprising monitoring means operatively connected to said second end of said secondary optical fiber for detecting and analyzing said fluorescent light passing back through said secondary optical fiber.

11. The endoscope apparatus of claim 8 wherein said observation means comprises a binocular microscope.

12. An endoscope apparatus for use in analyzing, treating, and diagnosing conditions within a body cavity comprising:

a flexible probe having an exterior surface, a medial portion, a first end, and a second end, said first end of said probe being sized for placement within said body cavity;

tissue potential sensing means positioned within said medial portion of said probe for receiving electrical potentials from tissue materials within said body cavity, said tissue potential sensing means comprising at least one elongate electrically conductive metallic wire member positioned within said medial portion of said probe, with at least a portion of said wire member extending outwardly from said first end of said probe, said portion of said wire member being exposed so that said portion of said wire member can directly contact tissue materials;

steering means operatively attached to said exterior surface of said probe for manipulating and moving said probe within said body cavity, said steering means comprising a plurality of elongate bands each being comprised of piezoelectric material and affixed to said exterior surface of said probe between said first end of said probe and said second end of said probe, whereby application of electricity to said bands causes said bands and said probe having said bands thereon to move; and detection means for detecting and analyzing said electrical potentials from said tissue materials within said body cavity, said detection means being operatively connected to said tissue potential sensing means.

* * * * *